United States Patent [19]

Pless

[11] Patent Number: 5,316,948
[45] Date of Patent: May 31, 1994

[54] N4-METHYL-2'-DEOXYCYTIDINE 5'-TRIPHOSPHATE AND ITS USE IN POLYMERASE-CATALYZED NUCLEIC ACID SYNTHESES

[75] Inventor: Reynaldo Pless, Gaithersburg, Md.

[73] Assignee: Life Technologies, Inc., Gaithersburg, Md.

[21] Appl. No.: 941,370

[22] Filed: Sep. 4, 1992

[51] Int. Cl.$^5$ .................. C12P 19/34; C07H 19/06; C07H 19/073
[52] U.S. Cl. ...................... 435/91.2; 435/6; 536/78.5; 536/78.51; 536/78.4
[58] Field of Search ............... 435/91, 6; 536/27, 28, 536/29, 22.1, 23.1, 28.4, 28.5, 28.51; 514/50, 51, 49

[56] References Cited

U.S. PATENT DOCUMENTS 5,112,734  5/1992  Kramer et al. .................. 435/6

OTHER PUBLICATIONS

McConlogue et al. Nuc. Acids Res. 16(20): 9869, 1988.
Brimacombe et al. J. Chem. Soc (c) pp.588–592, 1966.
Brimacombe et al. (1966) J. Mol. Biol. 18:529–540.
Butkus et al. (1987) Nucl. Acids Res. 15:8467–8478.
Seela et al. (1982) Biochemistry 21:4338–4343.
Draper (1984) Nucl. Acids Res. 12:989–1002.
Barr, P. J. (1986) BioTechniques 4:428–432.
Mizusawa et al. (1986) Nucl. Acids Res. 14:1319–1324.
Fazarkerley et al. (1987) Nucl. Acids Res. 15:2191–2200.

Primary Examiner—Margaret Parr
Assistant Examiner—Paul Tran
Attorney, Agent, or Firm—Greenlee and Winner

[57] ABSTRACT

The present invention provides novel compounds, $N^4$-methylcytidine 5'-triphosphate ($N^4$-methyl-CTP) and $N^4$-methyl-2'-deoxycytidine 5'-triphosphate ($N^4$-methyl-dCTP). These compounds serve as substrates for RNA or DNA polymerases for incorporation of the $N^4$-methyl-C moiety into oligo- and polynucleotides. This is advantageous for certain purposes. For example, DNA sequence analysis using the standard dideoxy chain termination method can be carried out using $N^4$-methyl-dCTP in the reaction mixture instead of dCTP. In the gel electrophoresis separation of the resulting oligonucleotides, artifacts of band compression and band distention are eliminated. The novel compounds may also be useful in other applications of primer extension reactions, for example, nucleic acid amplification schemes that employ transcription reactions or RNA replicases.

6 Claims, 10 Drawing Sheets

```
                                                    T   A       C
                                                      A T G A C G G G C
                                                    T A T C G A C C C G C
                                                    5'—...AAAAAAC GGCTAAAATA.....—3'
                                                                 9641 DNA

G   A
            T C C G G T C G A T C G G
            G A C G G C T A G C C G G C    G   A
5'—...AGC GTTTTTTA.....—3'                T A   T
         8641 DNA                         A T   A T
                                   5'—...AGTG CGTAATCATGGT.....—3'
                                            M13mp7 DNA
```

FIG. I

FIG. 2a
ACGT

TTCAG
AAATA
GGCTA
GGGGC
TGACT
ATTAC
CAGTC
CGCCC
AAAAA

FIG. 2b
ACGT

FIG. 2c
ACGT

FIG.6d ACGT

FIG.6c ACGT

FIG.6b ACGT

FIG.6a ACGT

COMPR.

COMPR.

$N^4$-METHYL-2'-DEOXYCYTIDINE 5'-TRIPHOSPHATE AND ITS USE IN POLYMERASE-CATALYZED NUCLEIC ACID SYNTHESES

FIELD OF THE INVENTION

The invention relates to the field of polymerase-catalyzed nucleic acid syntheses, in particular DNA or RNA polymerase-catalyzed primer extension reactions. Applications include DNA sequencing and polymerase chain reactions.

BACKGROUND OF THE INVENTION

In the gel electrophoretic resolution of oligonucleotides synthesized by a DNA or RNA polymerase-catalyzed reaction, artifacts occur when local sequence permits areas of secondary structure to occur in single-stranded nucleic acids, even under nominally denaturing conditions.

Resolution of DNA sequencing reaction mixtures by electrophoresis through denaturing polyacrylamide gels is often locally impaired by irregularities in the spacing of the electrophoretic bands. This phenomenon usually occurs as "band compression", a reduction in the spacing between consecutive bands, which may render their correct reading impossible. Band compression in sequencing gels occurs when the corresponding local nucleotide sequence contains an inverted repeat, and it is thought to arise from formation of hairpin structures in the single-stranded DNA fragments, despite the presence of 7M urea in the polyacrylamide gel. To alleviate this problem, the dGTP in the synthesis mixtures has been substituted by 7-deaza-dGTP (Barr PJ et al. (1986) BioTechniques.4:428–432; Mizusawa S et al. (1986) Nucleic Acids Res. 14:1319–1324) or by dITP. However, the use of 7-deaza-dGTP does not lead to complete resolution of band compressions caused by extended inverted repeats (which give rise to particularly stable hairpin loops), and use of dITP often leads to false stops at G-sites.

In applications of a polymerase chain reaction, hairpin structures formed by nearby G:C-rich tracts of a single-stranded template can reduce the fidelity of copying, resulting in amplification of incomplete and of incorrect sequences when compared to the original template.

Replacement of cytosines by $N^4$-methylcytosines ($N^4$-methylC) in polynucleotides has been shown to lower the stability of the polynucleotide complexes. The reduced stability of the G.$N^4$-methylC pair, compared to the G.C pair, has been documented in short self-complementary oligonucleotides (Fazakerley GV et al. (1987) Nucleic Acids Res. 15:2191–2200; Butkus V et al. (1987) Nucleic Acids Res. 15:8467–8478). When those data are compared with the results obtained in a comparison of the melting temperatures of poly(G).poly(C) and poly(7-deazaG).poly(C) (Seela F et al. (1982) Biochemistry 21:4338–4343), the destabilization imparted to the G.C base pair by $N^4$-methylation of the cytosine appears to be much greater than the destabilization of the G.C pair caused by substituting 7-deazaguanine for guanine.

$N^4$-methyl-2'-deoxycytidine has been synthesized previously and incorporated into chemically synthesized oligonucleotides (Butkus et al., supra). Conversion of C residues in RNA to $N^4$-methylC has been reported by Draper DE (1984) Nucleic Acids Res. 12:989–1002.

The duplex poly(7-deazaG).poly(C) shows only slightly lower thermal stability, compared to poly(G).poly(C), with $T_m$ values of 74° C. and 75° C., respectively, measured in 0.2M sodium EDTA at pH 5.3 (Seela et al., supra). In contrast to this moderate effect, the destabilization of the G.C pair achieved by the substitution of $N^4$-methylcytosine for cytosine is more substantial: for the duplex formed from a fully self-complementary dodecadeoxyribonucleotide, conversion of only two base pairs from G.C to G.$N^4$-methylC resulted in a change of $T_m$ from 60° C. to 55° C., measured in 0.1M NaCl, 0.2 mM EDTA, at 0.24 mM total nucleotide concentration (Butkus et al., supra), and for the duplex formed from the hexamer d-CGCGCG, change of the two central base pairs from G.C to G.$N^4$-methylC is reported to depress the $T_m$ by about 19° C., measured in $D_2O$ solution containing 150 mM NaCl, 10 mM phosphate (pH 7.4), and 0.2 mM EDTA at 48 mM total nucleotide concentration (Fazakerley et al., supra). At the polynucleotide level, complete replacement of cytosines in poly(I).poly(C) by $N^4$-methylcytosines lowers the $T_m$ by at least 50° C., and 39% replacement of cytosines by $N^4$-methylcytosines results in a $T_m$ depression of 15° C. (Brimacombe RLC & Reese CB (1966) J. Mol. Biol. 18:529–540).

SUMMARY OF THE INVENTION

The present invention provides a novel compound, $N^4$-methylcytidine 5'-triphosphate ($N^4$-methyl-CTP) and $N^4$-methyl-2'-deoxycytidine 5'-triphosphate ($N^4$-methyl-dCTP). Both compounds serve as substrates for RNA or DNA polymerases, respectively, for incorporation of the $N^4$-methylC moiety into oligo- and polynucleotides. For example, DNA sequence analysis, using the standard dideoxy chain termination method, can be carried out using $N^4$-methyl-dCTP in the reaction mixture instead of dCTP. In the gel electrophoresis separation of the resulting oligonucleotides, artifacts of band compression and band distention are substantially reduced, even in circumstances where stable hairpin structures arising from palindromic G:C-rich tracts cannot be resolved by the use of 7-deazaguanine. Assessing the deoxyribonucleotide analogues which are widely being used to counteract band compressions, the 7-deazaguanine substitution is not destabilizing enough in many instances, while the hypoxanthine substitution, in contrast, is too strongly destabilizing, leading to pronounced false stops. The $N^4$-methylcytosine substitution is intermediate in this regard, and will be beneficial in most cases.

The novel $N^4$-methyl-dCTP is also suitable for use in other applications of primer extension reactions, for example a polymerase chain reaction (PCR). The PCR experiments disclosed herein have demonstrated that Taq DNA polymerase tolerates the $N^4$-methylcytosine moiety not only in the nucleoside triphosphate substrate, but also simultaneously in the template strand. Similarly, the novel $N^4$-methyl-CTP is suitable for use in nucleic acid amplification schemes that employ transcription reactions or RNA replicases (see, e.g., International Publication Number WO 88/10315; EPO publication 0 310 229 A1).

DETAILED DESCRIPTION OF THE INVENTION

The invention provides novel $N^4$-methyl-dCTP and also N4-ethyl-dCTP and other related compounds useful in DNA polymerase-catalyzed primer extension reactions. By incorporating a compound of the invention into DNA, artifacts of band compression and band distention are ameliorated or removed altogether. Under certain circumstances artifacts due to false stops during the polymerase catalyzed reaction are encountered using $N^4$-methyl-dCTP. False stops can occur when the binding of the product strand to the template is destabilized by incorporation of $N^4$-methyl-dCTP and a hairpin exists in the template secondary structure. Such false stops are particularly apparent using the Sequenase ™ enzyme (exonuclease- T7 DNA polymerase). Use of Taq polymerase does not result in significant false stops, except in the case of extraordinarily stable hairpin structures. In general, use of elevated reaction temperatures tends to reduce the incidence of false stops regardless of the polymerase enzyme employed.

$N^4$-methyl-dCTP has therefore proven unexpectedly useful as a substituent for dCTP where reduced stability of localized secondary structures is desired. Although known destabilizing substituents have been employed for such purposes, none have proven entirely satisfactory. For example 7-deaza-G is too weakly destabilizing to be effective in many instances. At the other extreme, incorporation of hypoxanthine is too destabilizing, resulting in loss of fidelity in primer extension, and excessive false stops. The intermediate stability of $N^4$-methyl-dC substituents therefore unexpectedly strikes a balance of properties useful for a wide variety of primer extension-dependent processes.

Apart from its destabilization of potential hairpin structures, the substitution of $N^4$-methylcytosine for cytosine also affects the electrophoretic mobility of polynucleotides in another way: it produces a small, but significant retardation. The band spacings in sequencing ladders are known to correlate with the identity of the base added at each stage (Maxam AM & Gilbert W (1977) Proc. Natl. Acad. Sci. USA 74:560-564; Ambrose BJB & Pless RC (1985) Biochemistry 24:6194-6200), and the electrophoretic mobility of oligonucleotides in polyacrylamide gels is strongly dependent on the base composition (Frank R & Köster H (1979) Nucleic Acids Res. 15:2069-2087). The increased spacing caused by the N 4-methyl substitution increases the resolution in C-runs; this is beneficial because, among the canonical nucleotides, C is the one associated with the shortest band spacings (Maxam & Gilbert, supra; Ambrose & Pless, supra). The effect of the $N^4$-methyl substitution on the mobility of the polynucleotides dictates that sequencing reactions should not contain mixtures of dCTP and $N^4$-methyl-dCTP, as this would result in the formation of isostichs containing varying proportions of cytosines and $N^4$-methylcytosines, which would cause band broadening.

The sequencing experiments with Taq DNA polymerase showed that this enzyme efficiently utilizes $N^4$-methyl-dCTP as a substrate for DNA synthesis on a template containing canonical bases. In changing from dCTP to $N^4$-methyl-dCTP, a two-fold increase in concentration was sufficient to give satisfactory chain extension in the different lanes; however, the molar ratio of ddCTP to $N^4$-methyl-dCTP in the C-reaction had to be reduced considerably (compared to the ddCTP/dCTP ratio in the C-reaction using canonical nucleotides) to avoid premature average termination in the C-lane. Similar ratios were also used when 7-deaza-dGTP substituted for dGTP. The other polymerases, too, required only moderate adjustments in the nucleotide concentrations when the $N^4$-methylcytosine or 7-deazaguanine analogues were used.

Examination of space-filling models of B-form DNA indicates that other analogs of dCTP, bearing substituents at the N4 position, should perform similarly to $N^4$-methyl-dCTP, in DNA sequencing. Using such models, the following substitutions were tested on N4 of the cytosine in correctly formed C.G base pairs in B-DNA: $N^4$-methyl, $N^4$-ethyl, $N^4$-propyl, $N^4$-isopropyl, $N^4$-butyl, $N^4$-isobutyl, $N^4$-sec-butyl, $N^4$-tert-butyl. They were all found to be sterically possible, and it is clear that more extended chains can also be accommodated. However, an increase in substituent size beyond methyl should not afford any new advantage. Similar considerations apply with respect to the corresponding ribonucleotides. The $N^4$-methyl substitution is already sufficient to assure resolution of band compression in all instances, and a more bulky alkyl group may well increase the penchant for false stops in hairpin regions. The $N^4$,5-dimethylcytosine analogue is not a promising alternative, as poly($N^4$,5-dimethylC) failed to interact with poly(dI) (Zmudzka B et al. (1969) Biochemistry 8:3049-3059), probably due to steric interference between the two methyl groups in the configuration required for the formation of two H-bonds in the hypoxanthine.$N^4$,5-dimethylcytosine base pair.

A variety of useful kits comprising $N^4$-alkylcytidine 5'-triphosphate or $N^4$-alkyl-2'-deoxycytidine 5'-triphosphate can be assembled for ease and convenience in carrying out polymerase-catalyzed reactions to synthesize oligo- and polynucleotides having the novel compound incorporated therein. For example, a DNA sequencing kit can include $N^4$-alkyl-2'-deoxycytidine 5'-triphosphate, where alkyl is methyl, ethyl, propyl, isopropyl, butyl, isobutyl, sec-butyl, or tert-butyl in addition to dATP, dGTP, dTTP and the four dideoxy nucleotides, ddATP, ddGTP, ddTTP and ddCTP used as standard chain terminators. Conveniently, the alkyl moiety is methyl. Such kits can optionally contain 7-deaza-dGTP substituted for (or in addition to) dGTP. A kit of the basic type can also include 5-methyl-dCTP. Furthermore, kits having other C-terminators instead of ddCTP can be assembled, including any of 5-methyl-ddCTP, $N^4$-methyl-ddCTP, 3'-fluoro-ddCTP, 3'-amino-ddCTP or ara-CTP. A kit containing premixed reagents can be provided, including, for example, a first solution comprising dATP, dGTP, dTTP, $N^4$-alkyl-dCTP where alkyl is methyl, ethyl, propyl, isopropyl, butyl, isobutyl, sec-butyl or tert-butyl, and ddATP; a second solution comprising dATP, dGTP, dTTP, $N^4$-alkyl-dCTP where alkyl is methyl, ethyl, propyl, isopropyl, butyl, isobutyl, sec-butyl or tert-butyl, and ddCTP; a third solution comprising dATP, dGTP, dTTP, $N^4$-alkyl dCTP where alkyl is methyl, ethyl, propyl, isopropyl, butyl, isobutyl, sec-butyl or tert-butyl, and ddGTP; and a fourth solution comprising dATP, dGTP, dTTP, $N^4$-alkyl-dCTP where alkyl is methyl, ethyl, propyl, isopropyl, butyl, isobutyl, sec-butyl or tert-butyl, and ddTTP. A kit for performing a polymerase chain reaction includes dATP, dGTP, dTTP, $N^4$-alkyl-dCTP, where alkyl is methyl, ethyl, propyl, isopropyl, butyl, isobutyl, sec-butyl or tert-butyl and, optionally, dCTP. For carrying out RNA amplifications a kit comprising ATP, GTP, UTP and $N^4$-alkyl-cytidine 5'-triphosphate where alkyl is methyl, ethyl, propyl, isopropyl, butyl, isobutyl, sec-butyl or tert-butyl is provided.

The invention will be demonstrated in various embodiments set forth in the following Examples. The following general methods were used throughout.

The triethylammonium salt of $N^4$-methyl-dCTP was prepared in analogy to the published synthesis of $N^4$-aminoethyl-CTP (Draper, supra). 100 mg of dCTP (sodium salt, Sigma Chemical Company) was dissolved in 4.38 ml of an aqueous solution containing 5.29M methylammonium chloride, 0.01M methylamine, 2.4M sodium bisulfite, and 0.04% (w/v) hydroquinone. The solution, which had a pH of 6.5 at 25° C., was held for 18 h at 40° C. under a blanket of argon. The mixture was adjusted to pH 8.5 with aqueous NaOH and held at 25° C. for 2 h. After 100-fold dilution with water, the mixture was loaded onto a DEAE G-25 (bicarbonate form) column, which was then washed with water and eluted with a linear gradient of triethylammonium bicarbonate (0.01M to 1M). The appropriate fractions were pooled and desalted by repeated rotary evaporation with ethanol to afford a 35% yield of the desired material. The UV absorption spectra in aqueous solution at pH 10 ($\lambda_{max}=270$ nm, $\lambda_{min}=247$ nm) and at pH 2 ($\lambda_{max}=279$ nm, $\lambda_{min}=241$ nm) were close to those reported for the nucleoside (Wempen I et al. (1961) J. Amer. Chem. Soc. 83:4755-4766). For quantitation of $N^4$-methyl-dCTP in aqueous solution, the $\epsilon_{max}$ value (11,700 $M^{-1} cm^{-1}$ at 270 nm and pH 10) reported for the nucleoside (Wempen et al., supra) was used.

Enzymes were obtained from the following sources: Taq DNA polymerase for sequencing reactions and the large fragment of E. coli DNA polymerase I (Klenow fragment) from BRL, Sequenase TM from U.S. Biochemicals, Taq DNA polymerase for PCR (AmpliTaq TM) from Cetus.

[$\alpha$-$^{32}$P] dATP (3000 Ci/mmol) and [$^{35}$S]dATP$\alpha$S (650 Ci/mmol) were from Amersham.

Sequencing gel electrophoresis was performed in 6% or 8% polyacrylamide gels prepared from Gel-Mix 6 or Gel-Mix 8 (BRL).

M13mp19(+) strand DNA, M13mp7(+) strand DNA, pUC19 DNA, the M13 17-base primer, and the M13/pUC Forward 23-Base Sequencing Primer were the products of BRL. 864I DNA and 964I DNA were the gift of Dr. Deborah Polayes. HPV16/pT713 contains the entire HPV16 genome (7904 bp; Seedorf K et al. (1985) Virology 145:181-185) cloned into plasmid pT713 (2818 bp, BRL).

Sequencing reactions with Taq DNA polymerase were performed for 12 minutes at 72° C. The mixtures contained 60 μg/ml single-stranded template (i.e., 25 nM template), 0.10 μg/ml 23-base primer (i.e., 13 nM primer), 0.1 μM [$\alpha$-$^{32}$P]dATP, 25 mM Tris-HCl (pH 9.0 at 25° C.), 5 mM MgCl$_2$, 20 mM KCl, 2 mM dithiothreitol, 0.05% Triton X-100, and 33 U/ml Taq DNA polymerase. In addition, the various reaction tubes contained the nucleotide concentrations listed in Table I.

Sequencing reactions with Sequenase TM on single-stranded templates were performed according to the Sequenase TM protocol provided by the United States Biochemical Corporation. The termination reaction mixtures contained 8.4 μg/ml single-stranded template (i.e., 3.5 nM template), 0.58 μg/ml 23-base primer (i.e., 76 nM primer), 0.27 μM [$^{35}$S]dATPαS, 14 mM Tris-HCl (pH 7.5), 3.5 mM MgCl$_2$, 17.5 mM NaCl, and 113 U/ml Sequenase TM, and, in addition, the nucleotide concentrations listed in Table II.

For sequencing with Sequenase TM on a double-stranded template, pUC19 DNA was denatured by alkaline treatment (Chen EY & Seeburg PH (1985) DNA 4:165–170). Termination reaction mixtures had the same composition as used in sequencing of single-stranded DNA with Sequenase TM.

Sequencing with the large fragment of *E. coli* DNA polymerase I was performed essentially according to the KiloBase TM sequencing protocol of BRL. N$^4$-Methyl-dCTP was used instead of dCTP in the labeling-extension step preparatory to the termination reactions using N$^4$-methyl-dCTP. The termination reaction mixtures contained 39 μg/ml M13mp19(+) DNA (i.e., 15.5 nM template), 0.11 μg/ml 17-base primer (i.e., 19.5 nM primer), 22 mM Tris-HCl (pH 8.0), 5 mM MgCl$_2$, 25 mM NaCl, 3.65 mM dithiothreitol, 0.56 μM [$^{35}$S]dATPαS, 55 U/ml large fragment of *E. coli* DNA polymerase I, and, in addition, the nucleotide concentrations listed in Table III.

PCR amplification was carried out in solutions containing 200 μM dATP, 200 μM dCTP or N$^4$-methyl-dCTP, 200 μM dGTP, 200 μM dTTP, two primers (5'-GGTCGATGTATGTCTTGTTG-3'(SEQ ID NO:1) and 5'-GTCTACGTGTGTGCTTTGTAC-3' (SEQ ID NO:2), each at 1 μM concentration), HPV16/pT713 at 0.1 ng/ml (i.e., 0.014 pM plasmid), 50 mM KCl, 10 mM Tris-HCl (pH 8.3), 1.5 mM MgCl$_2$, 0.01% (w/v) gelatin, and 6 units/ml AmpliTaq TM enzyme. The solutions were overlaid with mineral oil and subjected to 25 cycles of either a high-temperature regimen (1 min at 94° C., 2 min at 55° C., 3 min at 72° C.) or a low-temperature regimen (1 min at 94° C., 2 min at 37° C., 3 min at 55° C.). The resulting mixtures were resolved by electrophoresis through a 2% agarose gel, followed by visualization with ethidium bromide and UV irradiation.

Figure 1:
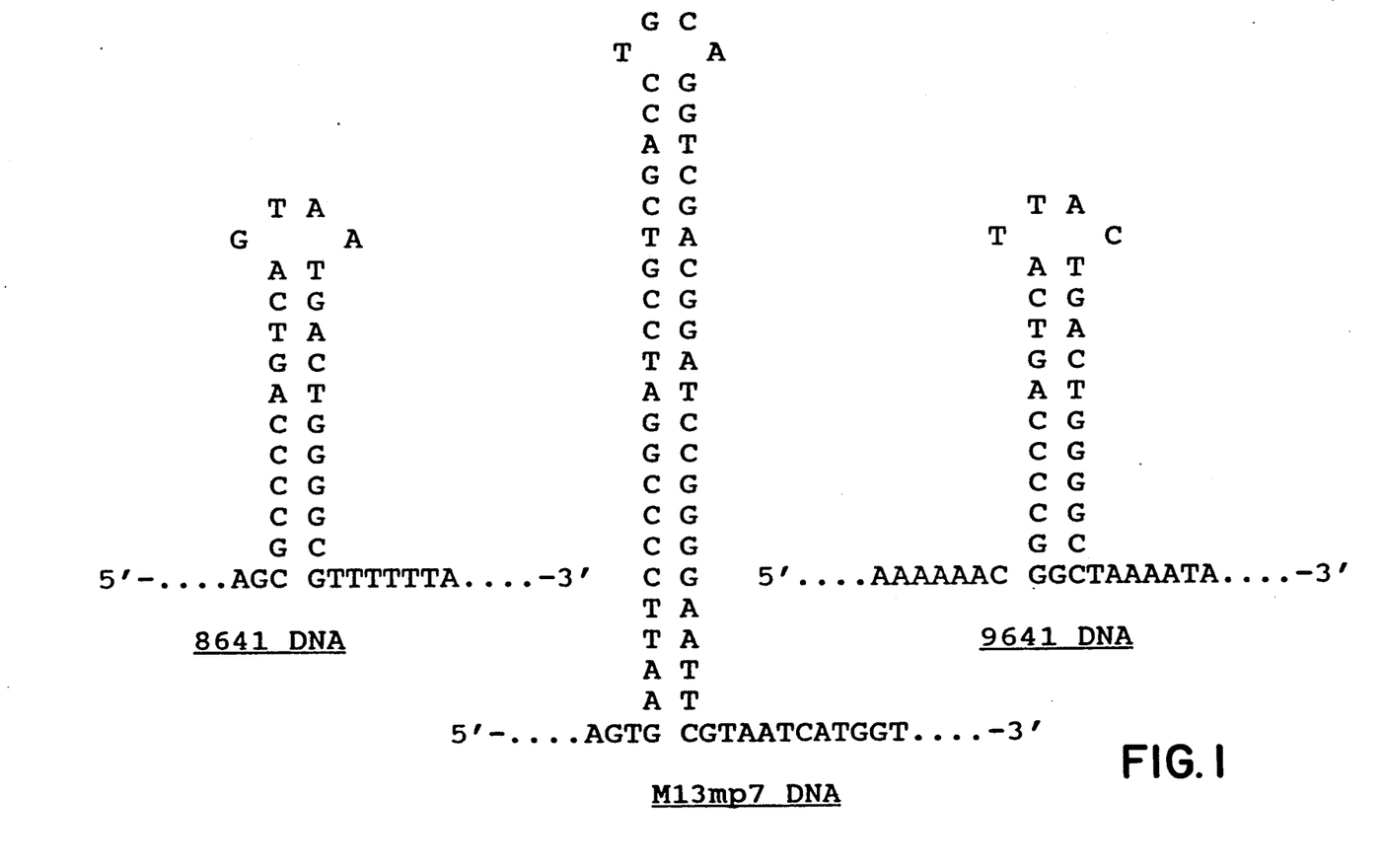
FIG. 1 shows local sequences containing inverted repeats used in the experiments disclosed herein, showing the hairpin structures. In each case the newly synthesized strand is shown.

As examples of templates leading to strong band compressions in the sequencing gels we chose 864I (see SEQ ID NO:3) DNA and 964I (see SEQ ID NO:5) DNA. In these DNAs, a 133-bp insert containing an inverted repeat is located in the multiple cloning sites of M13mp8/pUC8 and M13mp9/pUC9, respectively; the two constructs contain the identical insert in opposite orientations. In each case, the single-stranded template (and the corresponding newly synthesized fragments formed in the dideoxy terminator sequencing reactions) can form a double-stranded stem of eleven successive correctly matched base pairs, of which eight are G.C pairs, culminating in a four-nucleotide hairpin loop. The local sequences containing the inverted repeats are shown in FIG. 1 for the newly synthesized DNA (i.e., these sequences are complementary to the single-stranded templates). The inverted repeat within 864I DNA has SEQ ID NO:3, that of M13mp7 has SEQ ID NO:4 and that of 964I DNA has SEQ ID NO:5.

EXAMPLE 1

Figure 2A:
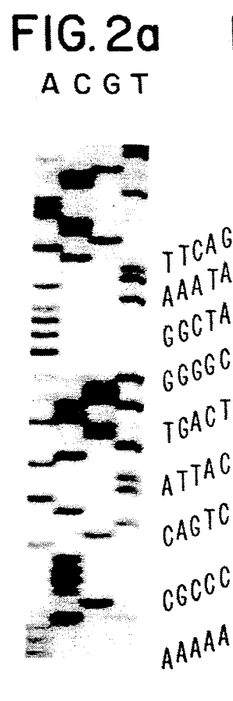
FIG. 2 is a sequencing gel obtained using Taq DNA polymerase on a single-stranded template of 964I DNA (see SEQ ID NO:5). In set (a) the sequencing ladders were obtained with dATP, dCTP, dGTP and dTTP; in set (b) with dATP, $N^4$-methyl-dCTP, dGTP and dTTP; in set (c) with dATP, dCTP, 7-deaza-dGTP and dTTP. Band identifications are given for set (b).
Figure 2B:
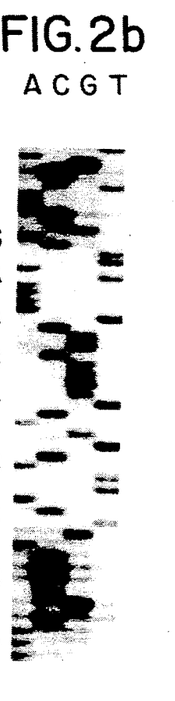
Figure 2C:
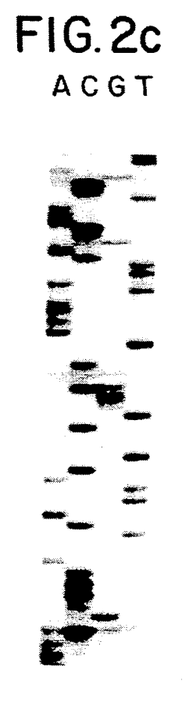
Figure 3A:
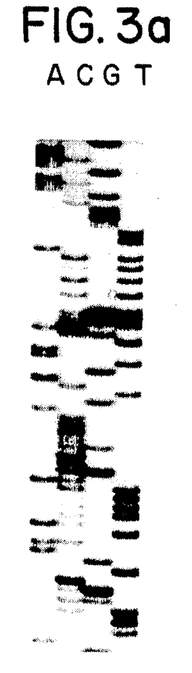
FIG. 3 is a sequencing gel obtained with Taq DNA polymerase on a single-stranded template of 864I (see EQ ID NO:3) DNA. Set (a): dATP, dCTP, dGTP, and dTTP; set (b): dATP, $N^4$-methyl-dCTP, dGTP, and dTTP; set (c): dATP, dCTP, 7-deaza-dGTP, and dTTP; set (d): dATP, $N^4$-methyl-dCTP, 7-deaza-dGTP, and dTTP; set (e): dATP, dCTP, dITP, and dTTP. Band identifications are given for set (c).
Figure 3B:
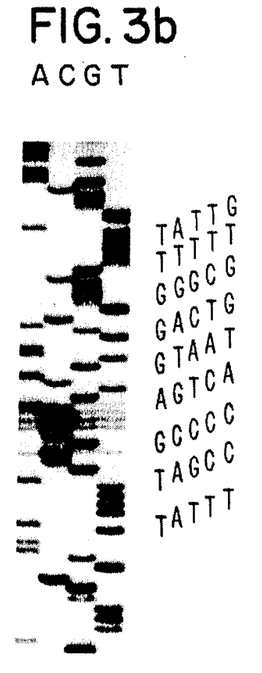
Figure 3C:
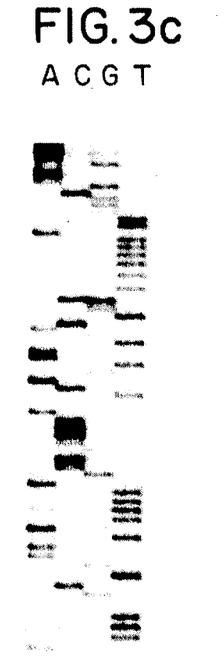
Figure 3D:
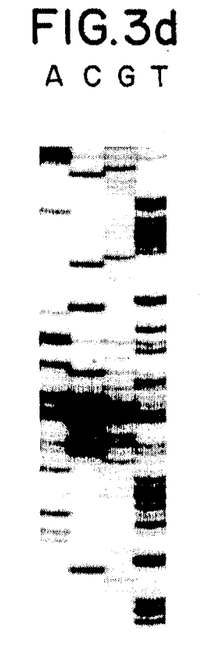
Figure 3E:
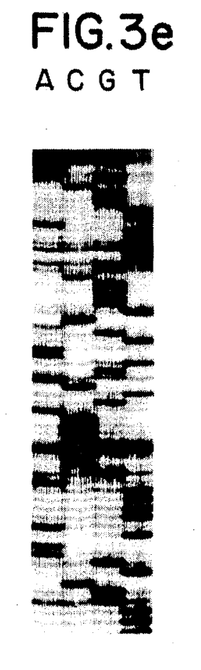

Dideoxy sequencing using Taq polymerase on a single-stranded template of 964I DNA (see SEQ ID NO:5). Dideoxynucleotide terminator reaction mixtures with Taq DNA polymerase at 72° C. contained the dNTP concentrations and ddNTP concentrations listed in Table I. The ddNTP/dNTP ratios were adjusted to give long extension (to >500 nucleotides from the labelled 5'-end), with approximately equal length in all four lanes. FIG. 2 shows the sequencing ladders for the region encompassing the inverted repeat in 964I DNA. For the set of reactions using N$^4$-methyl-dCTP instead of dCTP, the sequence is readable throughout, and all band spacings are regular. In contrast, the polymerization mixtures obtained with the canonical set of dNTPs (i.e., dATP, dCTP, dGTP, and dTTP) show severe band compression in the sequence GGGGCGGC (i.e., in the putative stem sequence distal to the primer), followed by distinct distention of spacings in the subsequent region (i.e., in the sequence immediately past the hairpin). Qualitatively similar results were obtained in the set of reactions using 7-deaza-dGTP instead of dGTP; band compression is still severe in the sequence GGGCGGC (though some resolution is achieved by the use of the deaza analogue), and band distention is still manifest in the sequence TAA following the hairpin.

Two main effects can be seen in using N$^4$-methyl-dCTP in DNA sequencing: (1) reduced tendency for band compressions, due to the destabilization of the G.C pairs forming hairpin structures, and (2) an increased potential for false stops, if the polymerase proves unable to efficiently displace hairpin structures in the template while it is newly forming only weak G.N$^4$-methylC pairs. On the electrophoretic ladder both effects appear in close proximity; for the rules of complementarity dictate that if the newly synthesized strand contains a region conducive to hairpin formation (causing band compression) the corresponding region in the template strand has a similar propensity for hairpin formation (causing false stops).

The DNA fragments synthesized in the presence of N$^4$-methyl-dCTP appear to be fully denatured under the conditions of sequencing gel electrophoresis, as seen by the resolution of band compression even in the most extreme case tested (a potential hairpin containing 22 base pairs). With hairpin structures of weak stability, both 7-deazaguanine substitution and N$^4$-methylcytosine substitution effected full resolution of band compressions. With stronger hairpin structures, however, the 7-deazaguanine analogue is ineffective in bringing about resolution of the band compression. This is shown in the present work on hairpins containing 11 base pairs (FIG. 2 and FIG. 3), but it is already well-known to be a problem in much less extreme cases (e.g., Mizusawa et al., supra).

In FIG. 2, in the set of lanes corresponding to the experiment involving N$^4$-methyl-dCTP, a series of false stops is seen at the beginning of the proximal complementary sequence of the hairpin (sequence CGCCCCAG) ; these false stops, however, are too weak to interfere with the reading of the sequence. False stops in this region are also seen for the reaction mixtures obtained with the canonical set of dNTPs or with the use of 7-deaza-dGTP, but they are less pronounced than the false stops seen in the mixtures obtained with N$^4$-methyl-dCTP. These stops probably arise from the hesitation of the DNA polymerase as it meets the hairpin structure in the template.

EXAMPLE 2

Dideoxy sequencing using Taq DNA polymerase on a single-stranded template of 864I DNA (see SEQ ID NO:3). FIG. 3 shows the sequencing autoradiogram for the hairpin region in 864I DNA (SEQ ID NO:3). Again, severe band compression and band distention are seen for the reaction mixtures obtained with the canonical set of dNTPS; these phenomena are alleviated, but not eliminated by the use of 7-deaza-dGTP, while the use of $N^4$-methyl-dCTP results in completely regular band spacings throughout the region. Use of both analogues, $N^4$-methyl-dCTP and 7-deaza-dGTP, in the same set of mixtures results in regular spacing, as expected, but also in an increased propensity for false stops and highly variable band intensities along one lane. Replacement of dGTP by dITP produces regular spacing throughout, but leads to a much increased background and pronounced false stops.

Figure 4A:
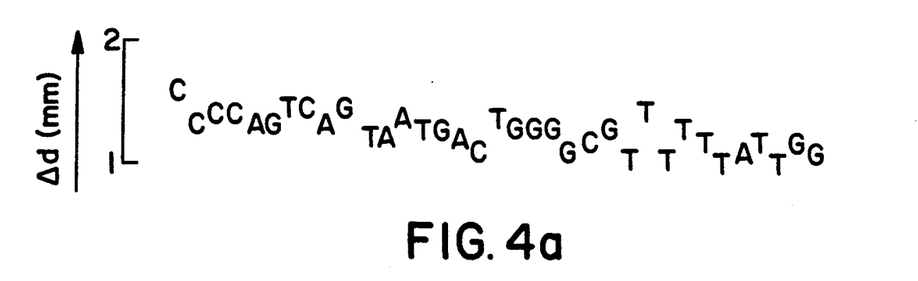
FIG. 4 shows the spacing of the electrophoretic bands measured for the region containing the inverted repeat in 864I DNA (see SEQ ID NO:3). For each band, the separation ($\Delta$d) from the next lower band in the ladder is given. The bands are identified by the base for which they stand. The 5'$\rightarrow$31' direction is from left to right. In panel (a), the sequencing ladders were obtained with dATP, $N^4$-methyl-dCTP, dGTP, and dTTP; in panel (b), with dATP, dCTP, dGTP, and dTTP; in panel (c), with dATP, dCTP, 7-deaza-dGTP, and dTTP.
Figure 4B:
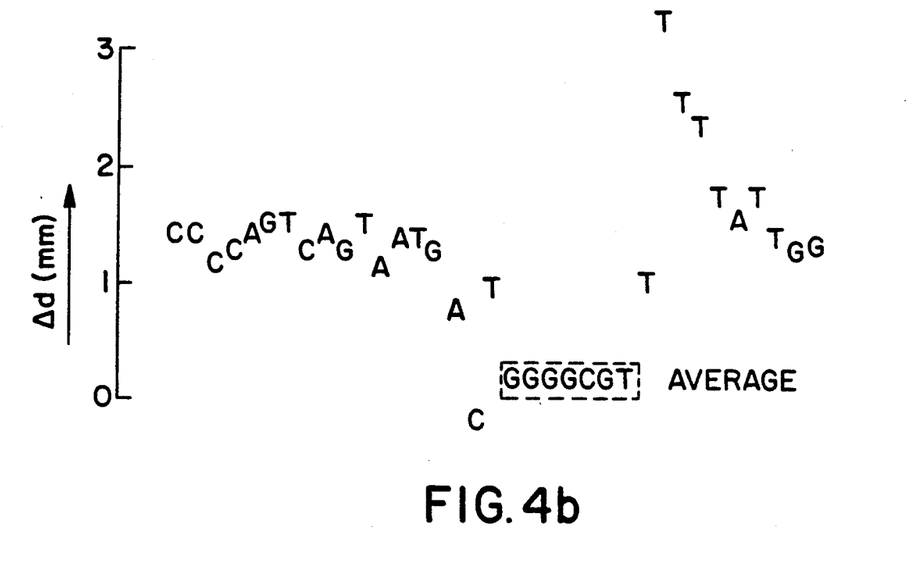
Figure 4C:
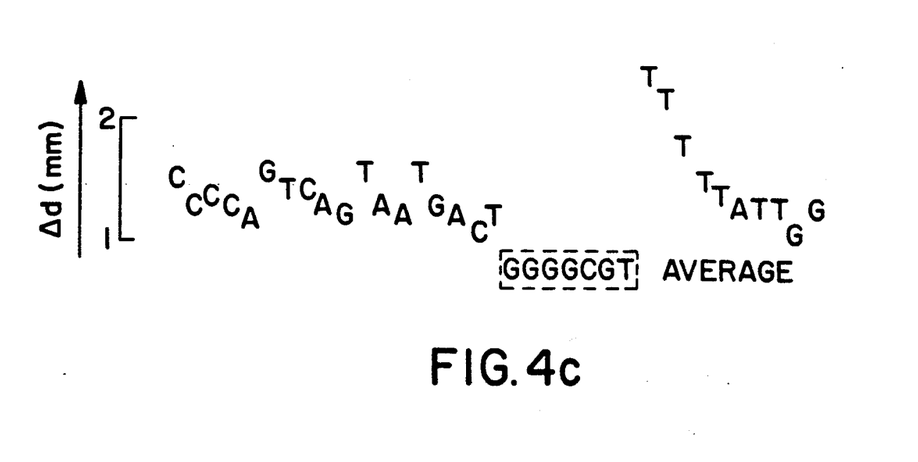
Figure 5A:
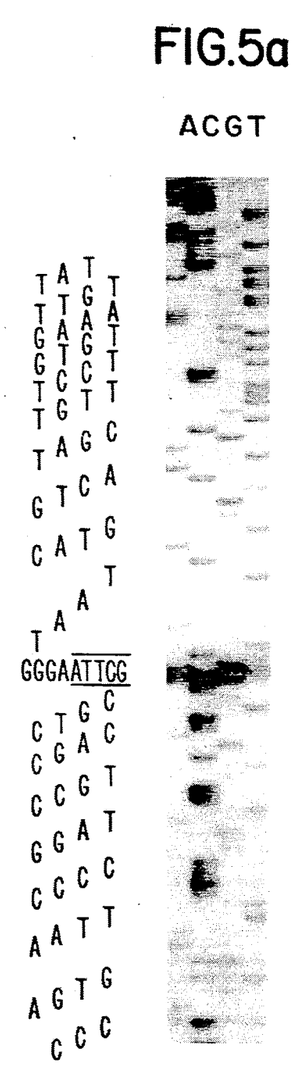
FIG. 5 is a sequencing gel obtained with Taq DNA polymerase on a single-stranded template of M13mp7 DNA (see SEQ ID NO:4). Set (a): dATP, dCTP, dGTP, and dTTP; set dATP, dCTP, 7-deaza-dGTP, and dTTP; sets (c), (d), and (e): dATP, $N^4$-methyl-dCTP, dGTP, and dTTP. In set (c) the nucleotide concentrations given in Table I were used; in sets (d) and (e), all nucleotide concentrations were raised four-fold and 10-fold, respectively.
Figure 5B:
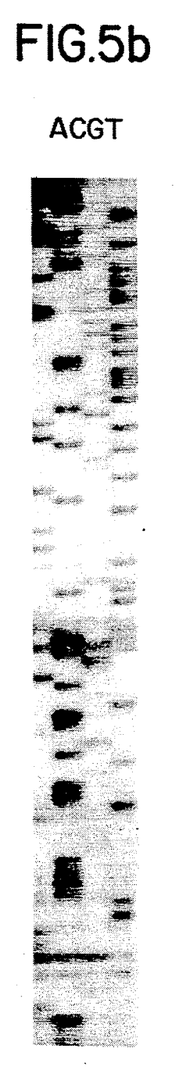
Figure 5C:
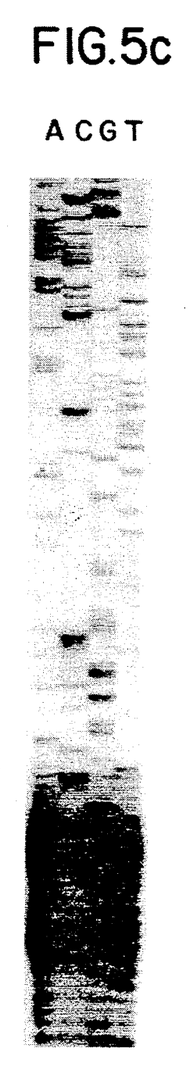
Figure 5D:
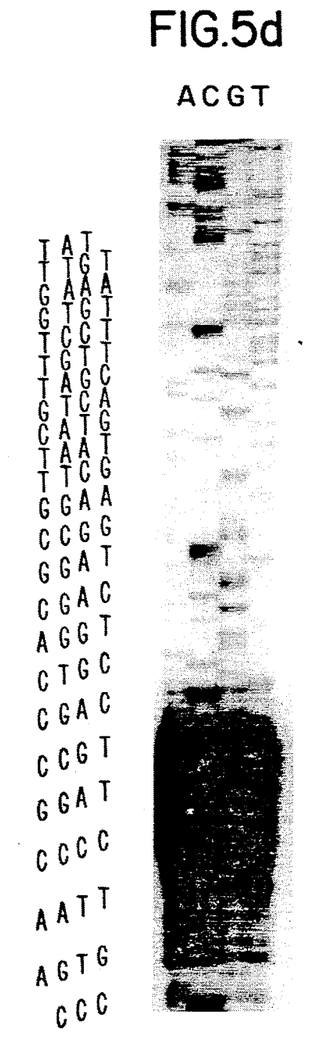
Figure 5E:
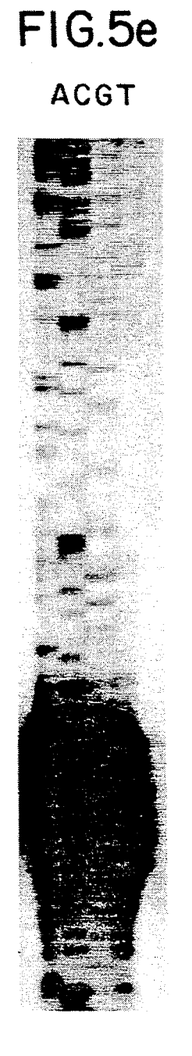
Figure 6A:
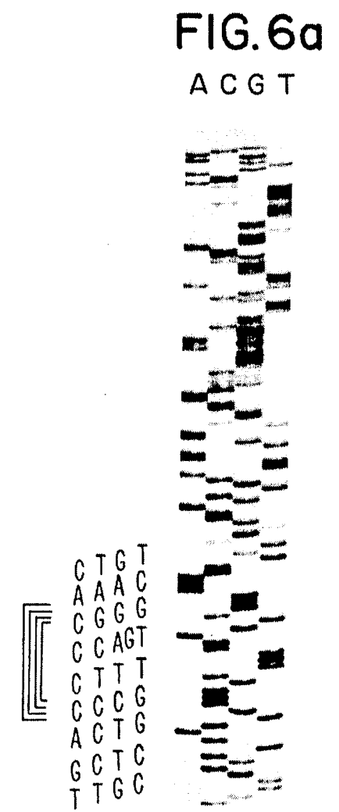
FIG. 6 is a sequencing gel obtained with Sequenase ™ (United States Biochemical, Cleveland, Ohio) on a single-stranded template of M13mp19 (see SEQ ID NO:4) DNA. Set (a): dATP, dCTP, dGTP, and dTTP; set (b): dATP, $N^4$-methyl-dCTP, dGTP, and dTTP; set (c): dATP, $N^4$-methyl-dCTP, 7-deaza-dGTP, and dTTP; set (d): dATP, dCTP, 7-deaza-dGTP, and dTTP.
Figure 6B:
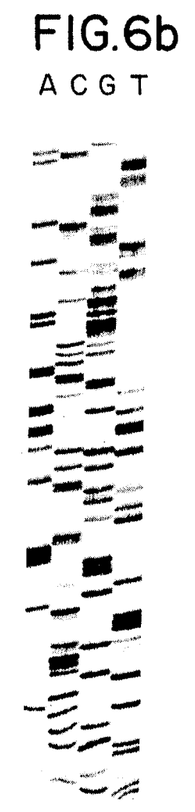
Figure 6C:
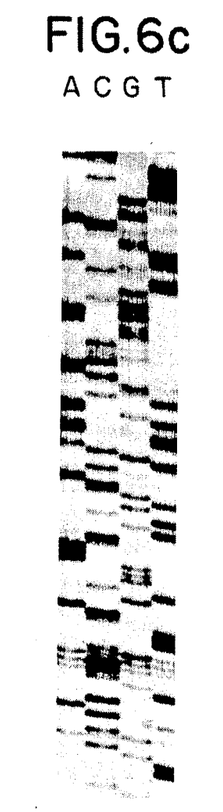
Figure 6D:
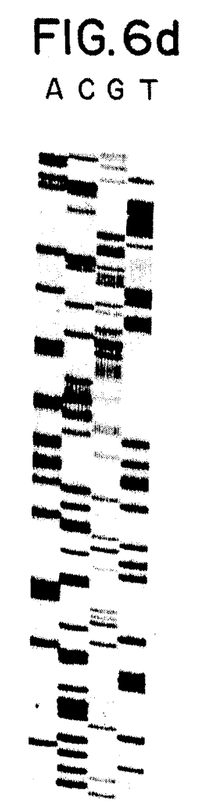
Figure 7A:
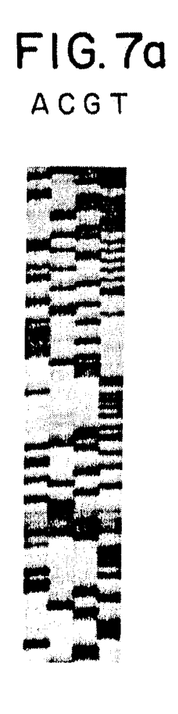
FIG. 7 is a sequencing gel obtained with Sequenase ™ on a single-stranded template of 864I (see SEQ ID NO:3) DNA. Set (a): dATP, dCTP, dGTP, and dTTP; sets (b), (d), (e), and (f): dATP, $N^4$-methyl-dCTP, dGTP, and dTTP; set (c): dATP, dCTP, 7-deaza-dGTP, and dTTP. In set (b) the nucleotide concentrations given in Table II were used; in sets (d), (e), and (f), all nucleotide concentrations were raised five-fold, 10-fold, and 30-fold, respectively.
Figure 7B:
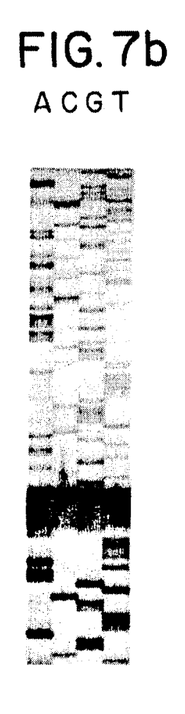
Figure 7C:
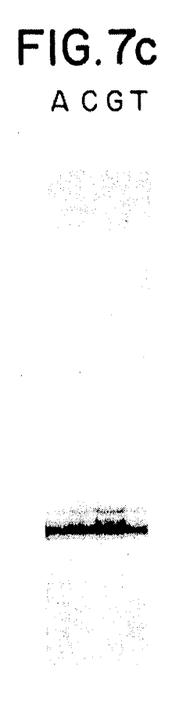
Figure 7D:
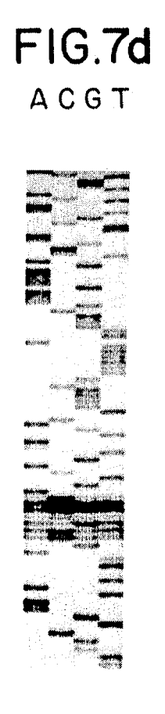
Figure 7E:
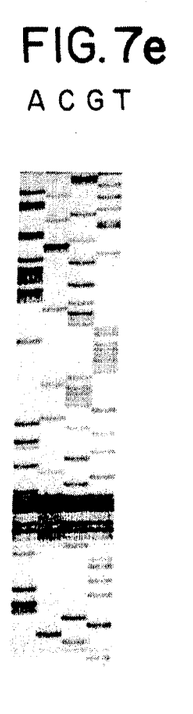
Figure 7F:
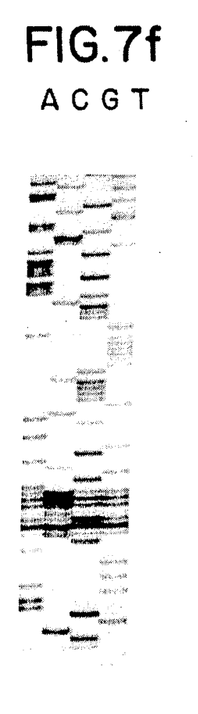

For a more quantitative evaluation, FIG. 4 presents the peak-to-peak distances of successive electrophoretic bands for sequencing reaction mixtures obtained on the 864I DNA template (see SEQ ID NO:3) For the reaction mixtures obtained with $N^4$-methyl-dCTP, regular spacing is observed throughout the potential hairpin region. Reaction mixtures obtained with the canonical set of dNTPs show regular spacing for fragments extending through the proximal segment of the potential stem region and the loop region, but show drastically reduced spacing as the fragments extend into the distal stem sequence and hence can form hairpin structures; band interpretation here is so unclear that only an average mobility decrease (barely larger than zero) can be given for a sequence of seven nucleotides. In the region immediately following the hairpin, band spacing is dramatically increased for several bands, reaching in one instance almost thrice the normal value. The set of reaction mixtures obtained with the 7-deazaguanine nucleotide shows a higher average band spacing in the unresolved region (GGGGCGT) and less prominent band distention after it.

EXAMPLE 3

Dideoxy sequencing using Taq DNA polymerase on a single-stranded template of 864I DNA (see SEQ ID NO:3). When M13mp7 DNA, which contains a region capable of forming a yet stronger hairpin structure (SEQ ID NO:4), was sequenced with Taq DNA polymerase and $N^4$-methyl-dCTP, very strong false stops were seen at the beginning of the proximal stem sequence (FIG. 5). The local sequence of the newly synthesized strand is shown in FIG. 1; this sequence can form a hairpin with 22 correct consecutive base pairs in the stem (14 of which would be G.C pairs) and a four-nucleotide loop. In this case, even the reaction sets using the canonical dNTPs or using 7-deaza-dGTP for dGTP showed marked false stops at the beginning of the hairpin. With the canonical set of dNTPs, there is an unresolved region containing 24 bands, followed by an extensive region of distended band spacings (for approximately 32 bands). Band compression and band distention are slightly alleviated with the use of the 7-deazaguanine analogue. In contrast, use of the $N^4$-methylcytosine analogue appears to preserve correct spacing through the hairpin region, but the bands beyond the strong false stops are weak and, in the region corresponding to the distal stem sequence, very diffuse. When all nucleotide concentrations in the $N^4$-methyl-dCTP set were raised four-fold, no reduction in the false stops was noted, but the bands in the region beyond these stops became stronger. A further increase in the nucleotide concentrations to 10-fold the original values did not further improve the sequencing ladders.

EXAMPLE 4

Dideoxy sequencing using Sequenase ™ on a single-stranded template of M13mp19 DNA. FIG. 6 shows results obtained with Sequenase ™ on M13mp19 single-stranded DNA at 37° C., using the concentrations given in Table II and [$^{35}$S]dATP. Readable sequence is obtained with the canonical set of dNTPS, with the substitution of 7-deaza-dGTP for dGTP, and with the substitution of $N^4$-methyl-dCTP for dCTP; but in the latter case there is a greater propensity for false stops. Simultaneous use of 7-deaza-dGTP and $N^4$-methyl-dCTP leads to increased incidence of false stops.

EXAMPLE 5

Dideoxy sequencing using Sequenase ™ on a single-stranded template of 864I DNA (see SEQ ID NO:3). Use of the $N^4$-methylcytosine analogue led to strong false stops (FIG. 7) when Sequenase ™ was used at 37° C. to sequence the single-stranded 864I template, with its strong potential for hairpin formation. In this case, false stops were also strongly apparent with 7-deaza-dGTP, and weakly so with the canonical set of dNTPs. Increasing the nucleotide concentrations in the $N^4$-methyl-dCTP set five-fold did reduce the false stops and increase the signal intensity above the false stops; further increase in the nucleotide concentration to 10-fold or 30-fold the original values brought no further benefit.

EXAMPLE 6

Figure 8A:
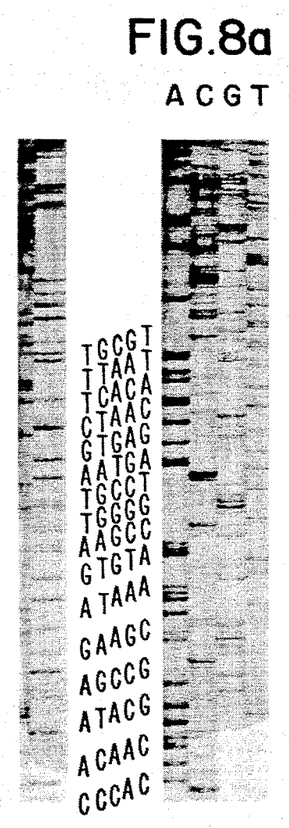
FIG. 8 is a sequencing gel obtained with the large fragment of E. coli DNA polymerase I on a single-stranded template of M13mp19 (see SEQ ID NO:4) DNA. Set (a): dATP, dCTP, dGTP, and dTTP; set (b): dATP, $N^4$-methyl-dCTP, dGTP, and dTTP.
Figure 8B:
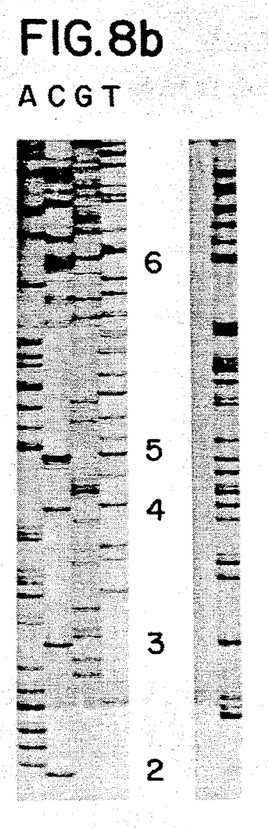

Dideoxy sequencing using the Klenow fragment of E. coli DNA polymerase I on a single-stranded template of M13mp19 DNA. Readable sequence was also obtained using $N^4$-methyl-dCTP on single-stranded M13mp19 template with the Klenow fragment of E. coli DNA polymerase I and [$^{35}$S]dATPaS. FIG. 8 shows the comparison with the data obtained using the canonical set of dNTPs.

EXAMPLE 7

Figure 9A:
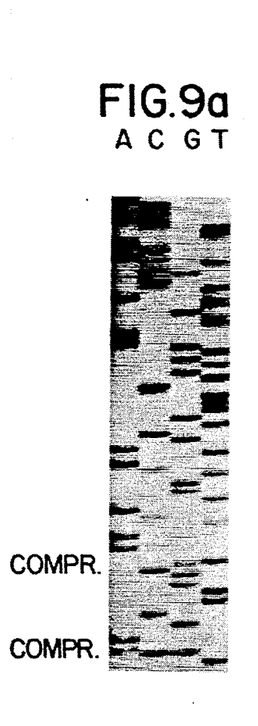
FIG. 9 is a sequencing gel obtained by double-stranded sequencing of pUC19 DNA with Sequenase ™. Set (a): dATP, dCTP, dGTP, and dTTP; set (b): dATP, dCTP, 7-deaza-dGTP, and dTTP; set (c): dATP, $N^4$-methyl-dCTP, dGTP, and dTTP.
Figure 9B:
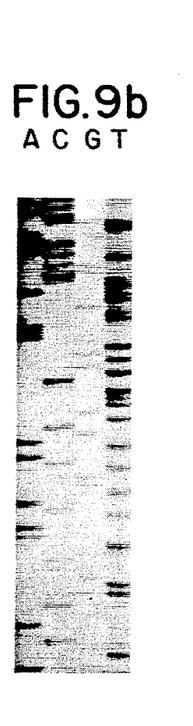
Figure 9C:
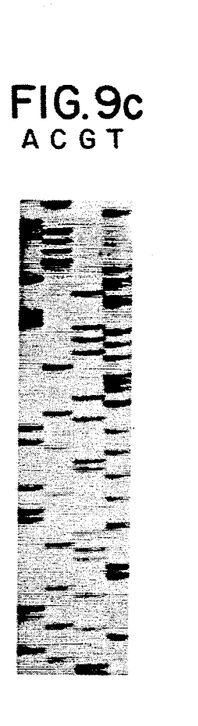

Sequence using double-stranded pUC19 DNA with Sequenase ™. Sequenase ™ and pUC19 DNA were used to test the $N^4$-methylcytosine analogue in sequencing of double-stranded DNA. As seen in FIG. 9, clear sequence information was obtained with the canonical nucleotides, with the substitution of 7-deaza-dGTP for dGTP, and with the substitution of $N^4$-methyl-dCTP for dCTP.

EXAMPLE 8

Figure 10:
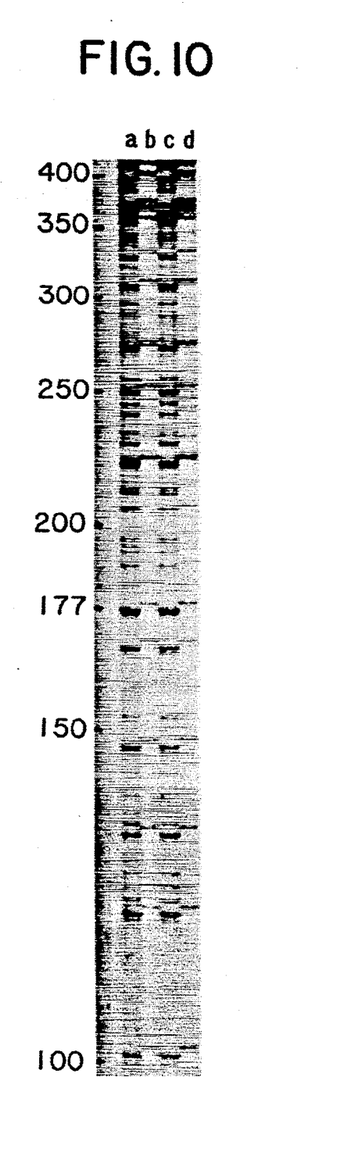
FIG. 10 is a side-by-side comparison of C-lanes obtained with the canonical set of dNTPs (lanes a and c) and with the substitution of $N^4$-methyl-dCTP for dCTP (lanes b and d). The reaction mixtures were obtained with the large fragment of E. coli DNA polymerase I on a single-stranded template of M13mp19 (see SEQ ID NO:4).

Side-by-side comparison of C-lanes comparing canonical dNTP's and $N^4$-methyl-dCTP substituted for dCTP. Substitution of $N^4$-methyl-dCTP for dCTP results in a distinct reduction in the electrophoretic mobility of the newly synthesized polynucleotides. A direct side-by-side comparison of electrophoretic lanes showed the polynucleotides containing $N^4$-methylcytosine to be off set from the cytosine containing polynucleotides by one nucleotide unit at the 100-mer stage, by three nucleotide units at the 250-mer stage, and by six nucleotide units at the 400-mer stage (FIG. 10), with each of these polynucleotides containing about 25% C. In line with this observation, direct measurement of the total spacing in C-runs unaffected by band compression or band distention gave values which were about 8% higher in electrophoretic lanes obtained with $N^4$-methyl-dCTP, compared to the lanes obtained with the canonical set of dNTPs. In contrast to the N⁴-methylcytosine analogue, the use of the 7-deazaguanine analogue does not noticeably affect band mobilities.

Substitution of N⁴-methyl-dCTP for dCTP does not cause a major alteration in the general rules which govern the variation of signal intensity along the electrophoretic lane. With Taq DNA polymerase, C-bands immediately following other C-bands stand out in the C-lane; this rule remains unchanged by the substitution of N⁴-methyl-dCTP for dCTP or of 7-deaza-dGTP for dGTP. Sequencing ladders obtained with Sequenase TM are characterized by more uniform band intensities along the lanes; this remains unaffected by the use of the N⁴-methylcytosine or 7-deazaguanine analogues. With the Klenow fragment of *E. coli* DNA polymerase I, the intensification of the second band in a run of Cs which is commonly observed with the canonical set of dNTPs is exaggerated with the use of N⁴-methyl-dCTP.

EXAMPLE 9

Use of N⁴-methyl-dCTP in PCR. To assess the potential for using N⁴-methyl-dCTP in PCR amplification, reaction mixtures containing the canonical nucleotide set were compared to mixtures in which dCTP was replaced by the N⁴-methylcytosine analogue, in a PCR experiment designed to amplify a 293 bp sequence of HPV16 DNA. Using a high-temperature regimen (1 min at 94° C., 2 min at 55° C., 3 min at 72° C., 25 cycles) the desired fragment was obtained with the canonical dNTPs, but not with N⁴-methyl-dCTP. A low-temperature regimen (1 min at 94° C., 2 min at 37° C., 3 min at 55° C., 25 cycles), conducted with dCTP or with N⁴-methyl-dCTP in the reaction mixture, cleanly produced identical amounts of the expected fragment as the sole amplification product.

While the invention has been described with reference to specific examples, its applicability is not to be treated as limited thereto. Those skilled in the art, having in mind the teachings and principles disclosed herein, will recognize advantages of the novel compounds of the invention and their use in other ways. In particular, any use that exploits the reduced thermodynamic stability of nucleic acid base-pairing interactions of a nucleic acid having a compound of the invention incorporated therein is deemed included in the invention.

TABLE I

| Nucleotide concentrations ($\mu$M) in the sequencing reactions with Taq DNA polymerase | | | | | | | | |
|---|---|---|---|---|---|---|---|---|
| Canonical set | dATP | dCTP | dGTP | dTTP | ddATP | ddCTP | ddGTP | ddTTP |
| A-lane | 16 | 24 | 24 | 24 | 160 | — | — | — |
| C-lane | 24 | 16 | 24 | 24 | — | 176 | — | — |
| G-lane | 24 | 24 | 38 | 24 | — | — | 90 | — |
| T-lane | 24 | 24 | 24 | 8.8 | — | — | — | 150 |
| N⁴-methyl-dCTP | dATP | N⁴-me-dCTP | dGTP | dTTP | ddATP | ddCTP | ddGTP | ddTTP |
| A-lane | 16 | 48 | 24 | 24 | 160 | — | — | — |
| C-lane | 24 | 32 | 24 | 24 | — | 58 | — | — |
| G-lane | 24 | 48 | 38 | 24 | — | — | 90 | — |
| T-lane | 24 | 48 | 24 | 8.8 | — | — | — | 150 |
| 7-deaza-dGTP | dATP | dCTP | 7-deaza-dGTP | dTTP | ddATP | ddCTP | ddGTP | ddTTP |
| A-lane | 16 | 24 | 48 | 24 | 160 | — | — | — |
| C-lane | 24 | 16 | 48 | 24 | — | 176 | — | — |
| G-lane | 24 | 24 | 38 | 24 | — | — | 45 | — |
| T-lane | 24 | 24 | 48 | 8.8 | — | — | — | 150 |
| N⁴-methyl-dCTP + 7-deaza-dGTP | dATP | N⁴-me dCTP | 7-deaza-dGTP | dTTP | ddATP | ddCTP | ddGTP | ddTTP |
| A-lane | 16 | 48 | 76 | 24 | 176 | — | — | — |
| C-lane | 24 | 32 | 76 | 24 | — | 58 | — | — |
| G-lane | 24 | 48 | 76 | 24 | — | — | 45 | — |
| T-lane | 24 | 48 | 76 | 8.8 | — | — | — | 150 |
| dITP | dATP | dCTP | dITP | dTTP | ddATP | ddCTP | ddGTP | ddTTP |
| A-lane | 16 | 24 | 48 | 24 | 160 | — | — | — |
| C-lane | 24 | 16 | 48 | 24 | — | 176 | — | — |
| G-lane | 24 | 24 | 76 | 24 | — | — | 45 | — |
| T-lane | 24 | 24 | 48 | 8.8 | — | — | — | 150 |

TABLE II

| Nucleotide concentrations ($\mu$M) in the sequencing reactions with Sequenase TM | | | | | | | | |
|---|---|---|---|---|---|---|---|---|
| Canonical set | dATP | dCTP | dGTP | dTTP | ddATP | ddCTP | ddGTP | ddTTP |
| A-lane | 40 | 40 | 40 | 40 | 4 | — | — | — |
| C-lane | 40 | 40 | 40 | 40 | — | 4 | — | — |
| G-lane | 40 | 40 | 40 | 40 | — | — | 4 | — |
| T-lane | 40 | 40 | 40 | 40 | — | — | — | 4 |
| N⁴-methyl-dCTP | dATP | N⁴-me-dCTP | dGTP | dTTP | ddATP | ddCTP | ddGTP | ddTTP |
| A-lane | 40 | 80 | 40 | 40 | 4 | — | — | — |
| C-lane | 40 | 80 | 40 | 40 | — | 0.4 | — | — |
| G-lane | 40 | 80 | 40 | 40 | — | — | 4 | — |
| T-lane | 40 | 80 | 40 | 40 | — | — | — | 4 |
| 7-deaza- | | | | | | | | |

TABLE II-continued

Nucleotide concentrations (μM) in the sequencing reactions with Sequenase ™

| 7-deaza-dGTP | dATP | dCTP | dGTP | dTTP | ddATP | ddCTP | ddGTP | ddTTP |
|---|---|---|---|---|---|---|---|---|
| A-lane | 40 | 40 | 80 | 40 | 4 | — | — | — |
| C-lane | 40 | 40 | 80 | 40 | — | 4 | — | — |
| G-lane | 40 | 40 | 80 | 40 | — | — | 2 | — |
| T-lane | 40 | 40 | 80 | 40 | — | — | — | 4 |

| N⁴-methyl-dCTP + 7-deaza-dGTP | dATP | N⁴-me-dCTP | 7-deaza-dGTP | dTTP | ddATP | ddCTP | ddGTP | ddTTP |
|---|---|---|---|---|---|---|---|---|
| A-lane | 40 | 80 | 80 | 40 | 4 | — | — | — |
| C-lane | 40 | 80 | 80 | 40 | — | 0.4 | — | — |
| G-lane | 40 | 80 | 80 | 40 | — | — | 2 | — |
| T-lane | 40 | 80 | 80 | 40 | — | — | — | 4 |

TABLE III

Nucleotide concentrations (μM) in the termination reactions with the large fragment of *E. coli* DNA polymerase I

| Canonical set | dATP | dCTP | dGTP | dTTP | ddATP | ddCTP | ddGTP | ddTTP |
|---|---|---|---|---|---|---|---|---|
| A-lane | 10.4 | 104 | 104 | 104 | 125 | — | — | — |
| C-lane | 104 | 10.4 | 104 | 104 | — | 20.8 | — | — |
| G-lane | 104 | 104 | 10.4 | 104 | — | — | 31.3 | — |
| T-lane | 104 | 104 | 104 | 10.4 | — | — | — | 104 |

| N⁴-methyl-dCTP | dATP | N⁴-me-dCTP | dGTP | dTTP | ddATP | ddCTP | ddGTP | ddTTP |
|---|---|---|---|---|---|---|---|---|
| A-lane | 10.4 | 104 | 104 | 104 | 125 | — | — | — |
| C-lane | 104 | 10.4 | 104 | 104 | — | 2.09 | — | — |
| G-lane | 104 | 104 | 10.4 | 104 | — | — | 63 | — |
| T-lane | 104 | 104 | 104 | 10.4 | — | — | — | 313 |

We claim:

1. In a method of DNA sequencing by primer extension comprising the steps of annealing a primer to a template and extending the primer using a DNA polymerase, wherein the improvement comprises using a mixture of deoxynucleoside triphosphates comprising $N^4$-methyl-2'-deoxycytidine 5'-triphosphate.

2. The method of claim 1, wherein said DNA polymerase is selected from the group consisting of Taq DNA polymerase, E. coli DNA polymerase I, the Klenow fragment of E. coli DNA polymerase I, and T7 DNA polymerase.

3. In a method of dideoxy DNA sequencing by primer extension comprising the steps of annealing a primer to a template and extending the primer wherein the reaction mixture comprises a DNA polymerase, a mixture of deoxynucleoside triphosphates and a chain-terminating nucleoside triphosphate, and wherein the improvement comprises substituting $N^4$-methyl-2'-deoxycytidine 5'-triphosphate for deoxycytidine 5'-triphosphate.

4. The method of claim 3, wherein said DNA polymerase is selected from the group consisting of Taq DNA polymerase, E. coli DNA polymerase I, the Klenow fragment of E. coli DNA polymerase I, and T7 DNA polymerase.

5. In a method of nucleic acid amplification by primer extension comprising the steps of annealing a primer to a template and extending the primer using a DNA polymerase, wherein the improvement comprises using a mixture of deoxynucleoside triphosphates comprising $N^4$-methyl-2'-deoxycytidine 5'-triphosphate.

6. The method of claim 5, wherein said DNA polymerase is selected from the group consisting of Taq DNA polymerase, E. coli DNA polymerase I, the Klenow fragment of E. coli DNA polymerase I, and T7 DNA polymerase.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear    ( i i ) MOLECULE TYPE: DNA (genomic)

( x i ) SEQUENCE DESCRIPTION: SEQ ID NO:1:

GGTCGATGTA TGTCTTGTTG    20

( 2 ) INFORMATION FOR SEQ ID NO:2:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear    ( i i ) MOLECULE TYPE: DNA (genomic)

( x i ) SEQUENCE DESCRIPTION: SEQ ID NO:2:

GTCTACGTGT GTGCTTTGTA C    21

( 2 ) INFORMATION FOR SEQ ID NO:3:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear (i i) MOLECULE TYPE: DNA (genomic)

(x i) SEQUENCE DESCRIPTION: SEQ ID NO:3:

AGCGCCCCAG TCAGTAATGA CTGGGGCGTT TTTTA    35

(2) INFORMATION FOR SEQ ID NO:4:

(i) SEQUENCE CHARACTERISTICS:
 (A) LENGTH: 62 base pairs
 (B) TYPE: nucleic acid
 (C) STRANDEDNESS: single
 (D) TOPOLOGY: linear (i i) MOLECULE TYPE: DNA (genomic)

(x i) SEQUENCE DESCRIPTION: SEQ ID NO:4:

AGTGAATTCC CCGGATCCGT CGACCTGCAG GTCGACGGAT CCGGGGAATT CGTAATCATG    60

GT    62

(2) INFORMATION FOR SEQ ID NO:5:

(i) SEQUENCE CHARACTERISTICS:
 (A) LENGTH: 41 base pairs
 (B) TYPE: nucleic acid
 (C) STRANDEDNESS: single
 (D) TOPOLOGY: linear (i i) MOLECULE TYPE: DNA (genomic)

(x i) SEQUENCE DESCRIPTION: SEQ ID NO:5:

AAAAAACGCC CCAGTCATTA CTGACTGGGG CGGCTAAAAT A    41